US008666021B2

(12) United States Patent
Fadler

(10) Patent No.: US 8,666,021 B2
(45) Date of Patent: Mar. 4, 2014

(54) RADIATION THERAPY SYSTEM

(75) Inventor: Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 345 days.

(21) Appl. No.: 12/829,123

(22) Filed: Jul. 1, 2010

(65) Prior Publication Data
US 2011/0007867 A1    Jan. 13, 2011

(30) Foreign Application Priority Data

Jul. 9, 2009   (DE) .......................... 10 2009 032 430

(51) Int. Cl.
*A61N 5/10* (2006.01)
(52) U.S. Cl.
USPC .................................... 378/65; 378/4; 378/20
(58) Field of Classification Search
USPC .................................................. 378/4, 20, 65
See application file for complete search history.

(56) References Cited

U.S. PATENT DOCUMENTS

| 6,302,579 B1* | 10/2001 | Meyer et al. ................. 378/196 |
| 6,842,502 B2 | 1/2005 | Jaffray et al. |
| 2004/0024300 A1 | 2/2004 | Graf |
| 2004/0034438 A1* | 2/2004 | Uematsu ......................... 700/59 |
| 2006/0064008 A1 | 3/2006 | Moore |
| 2006/0163495 A1 | 7/2006 | Hiramoto et al. |
| 2007/0003021 A1 | 1/2007 | Guertin et al. |
| 2009/0097614 A1 | 4/2009 | Bergfjord et al. |

FOREIGN PATENT DOCUMENTS

| DE | 102006033501 A1 | 2/2007 |
| DE | 102007011399 A1 | 9/2008 |

OTHER PUBLICATIONS

German Office Action dated Feb. 25, 2010, for corresponding German Patent Application No. DE 10 2009 032 430.5, with English translation.

* cited by examiner

*Primary Examiner* — Hoon Song
(74) *Attorney, Agent, or Firm* — Lempia Summerfield Katz LLC

(57) ABSTRACT

A radiation therapy system including a radiation therapy apparatus for generating a therapeutic treatment beam, with which an object is irradiated, an imaging apparatus for generating a medical image of the object, and a positioning apparatus, with which the object is positioned in the radiation therapy system for irradiation and imaging purposes, is provided. The imaging apparatus and the radiation therapy apparatus are both rotatably mounted so that the object is positioned in a first rotation state in the imaging apparatus and is positioned in the radiation therapy apparatus in a second rotation state.

15 Claims, 2 Drawing Sheets

RADIATION THERAPY SYSTEM

This application claims the benefit of DE 10 2009 032 430.5, filed Jul. 9, 2009, which is hereby incorporated by reference.

BACKGROUND

The present embodiments relate to a radiation therapy system having a radiation therapy apparatus, an imaging apparatus and a positioning apparatus.

Radiation therapy systems of this type are used in the treatment of different diseases and enable a patient to be irradiated conventionally with x-ray radiation, electron radiation or other ionizing radiation.

Radiation therapy systems are known, in which a computer tomograph is mounted on rails and can be moved to and from the radiation therapy apparatus. A therapy table can be pivoted in such a system so that an imaging with the computer tomograph and an irradiation with the radiation therapy device is possible with the same therapy table.

Patient tables that are positioned using a robot arm to position the patient are also known in the art.

US 2007/0003021 A1 shows different possibilities of how a patient can be positioned in the radiation therapy apparatus and in a computer tomograph or a C-arm.

SUMMARY AND DESCRIPTION

The present embodiments may obviate one or more of the drawbacks or limitations in the related art. For example, in on embodiment, a radiation therapy system, in which both the imaging and the treatment are implemented with high levels of patient comfort and safety is provided.

The radiation therapy system of the one embodiment includes a radiation therapy apparatus for generating a therapeutic treatment beam, with which an object may be irradiated, an imaging apparatus for generating a medical image of the object, and a positioning apparatus, with which the object may be positioned in the radiation therapy system. The imaging apparatus and the radiation therapy apparatus may both be rotatably mounted so that the object may be positioned in a first rotation state in the imaging apparatus and may be positioned in a second rotation state in the radiation therapy apparatus.

For patient safety and comfort, it is advantageous to move the patient as little as possible while imaging and irradiating the patient.

In the radiation therapy system, the radiation therapy apparatus and the imaging apparatus form a shared, rotatably mounted unit. The alignment of the radiation therapy apparatus and the imaging apparatus may be changed with respect to the positioning apparatus. For imaging purposes, the imaging apparatus is rotated toward the positioning apparatus, so that the object to be irradiated (e.g., the patient or a phantom for monitoring and maintenance purposes) is further moved by a small amount in order to implement the imaging. A rotation of a unit including the radiation therapy apparatus and the imaging apparatus takes place using a swivel drive such as, for example, a crane, so that the radiation therapy apparatus is rotated toward the positioning apparatus. To implement an irradiation, the object is further moved to a minimal extent.

The rotatable mounting of the radiation therapy apparatus with the imaging apparatus on the swivel drive is advantageous in that the patient is not rotated as in known solutions. The patient is not secured specially during these movements. Patient comfort increases since large, passive movements may be perceived as unpleasant.

Excessively large movement of the positioning apparatus that necessitates measures to compensate for the movement-specific variable table deflection (e.g., particularly rigid table plates, expensive robotic positioning arms or intrinsic support mechanisms) is avoided. With conventional table constructions, large deviations may not be realized, since standards issued by the International Electrotechnical Commission (IEC) with respect to the deflection and radiation transparency have to be met. This problem is alleviated with the present embodiments, since the patient table for therapy and imaging implements a comparable movement.

The positioning apparatus of the radiation therapy system may be configured more simply and thus also more cost-effectively. The rotatable mounting of the radiation therapy apparatus and the imaging apparatus about a vertical axis is also advantageous in that the rotatable mounting is space-saving in comparison with solutions in which part of the radiation therapy system is moved linearly.

In one embodiment, the imaging apparatus is a tube such as, for example, a computer tomograph. With this embodiment, the object to be examined may be moved at least partially into the imaging apparatus (e.g., the tube) in order to produce an image. With the positioning apparatus configured as a patient table, for example, this is achieved by moving the patient table along the longitudinal axis of the patient table.

In one embodiment, the radiation therapy apparatus includes a circular structure with a central opening, into which the object may be at least partially moved by the positioning apparatus during the positioning process. This is also achieved by moving the patient table along the longitudinal axis of the patient table.

If both the radiation therapy apparatus and the imaging apparatus have a circular structure with a central opening, the two structures may be arranged one behind the other such that a channel is created, through which the object may be moved.

In one embodiment, the radiation therapy apparatus includes an overhanging arm that is operable to direct the therapeutic treatment beam at the object to be irradiated. The overhanging arm may, for example, be attached to a radiation therapy apparatus including a circular structure of the central opening or an L-shaped and/or C-shaped radiation therapy apparatus.

In one embodiment, the imaging apparatus of the radiation therapy apparatus may be arranged or mounted on a shared, rotatable foot on a circular base plate, for example. The foot may be rotatably mounted by way of a pivot bearing. The foot may be embedded into a surrounding base such that the base and foot are at the same height so that no step is created.

In another embodiment, the positioning apparatus may be mounted such that the positioning apparatus may be rotated about a vertical axis (e.g., by mounting on a separate, rotatable foot).

For the correct positioning of an object (e.g., the patient) an imaging data record may be recorded with an imaging apparatus (e.g., a 3D CT data record). Since the radiation therapy system has a fixed, defined distance between the radiation therapy apparatus and the imaging apparatus (e.g., as the result of a fixed, defined distance of the therapy beam and/or isocenter from the CT scan plane), the position of the patient may be very precisely synchronized and adjusted on the basis of the imaging data record using the therapy device. Control commands, which are used to control the positioning apparatus, may be determined and provided by a control apparatus of the radiation therapy system.

DETAILED DESCRIPTION OF THE DRAWINGS

Figure 1:
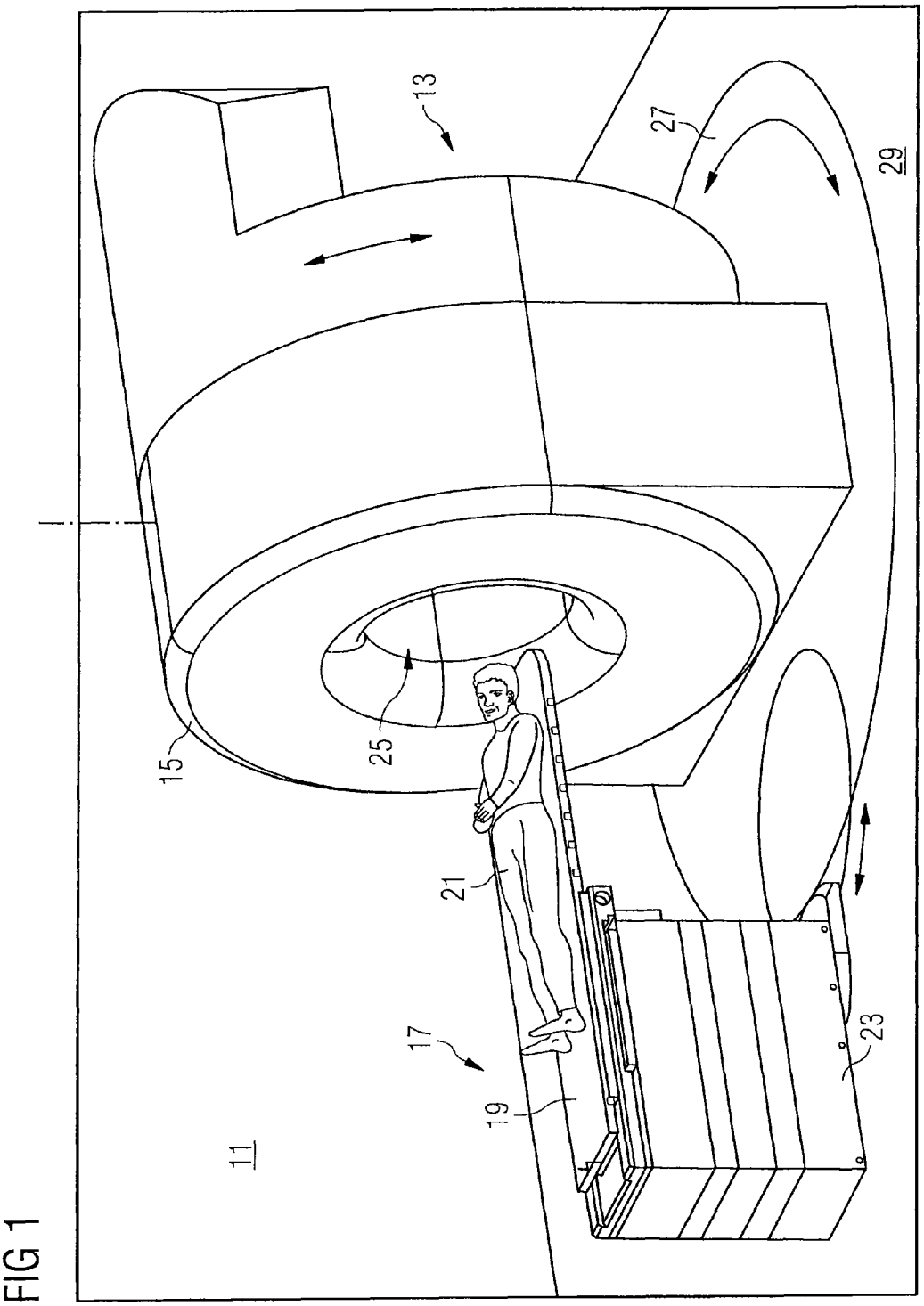
FIG. 1 shows one embodiment of a radiation therapy system in a rotational position for imaging.

FIG. 1 shows one embodiment of a radiation therapy system 11 in a rotational position for imaging. The radiation therapy system 11 includes a radiation therapy apparatus 13, an imaging apparatus 15 and a positioning apparatus 17.

In one embodiment, the radiation therapy apparatus 13 includes an apparatus for generating therapeutic x-ray and/or gamma radiation in the MV range (e.g., a linear accelerator) and a collimator for forming a cross-sectional profile of a therapeutic treatment beam. The radiation therapy apparatus may be rotated about a horizontal axis, so that the therapeutic treatment beam may be directed at an object to be irradiated from different solid angles.

With the imaging apparatus 15, an image of the interior of the object to be irradiated may be produced. Diagnostic x-ray radiation (e.g., in the kV range) is generated by an x-ray source and directed through the object onto an x-ray detector. Computer tomographs, cone beam CT devices and 2-D x-ray apparatuses, for example, are used.

The positioning apparatus 17 includes a patient table 19, on which a patient 21 may be positioned, and a support apparatus 23 for the patient table 19. In the embodiment shown in FIG. 1, the support apparatus 23 is an adjustable base that may be rotated about a separate vertical axis. The patient table 19 may be moved along the longitudinal axis of the patient table 19 to move the patient 21 onto the radiation therapy apparatus 13 and/or imaging apparatus 15.

In the embodiment shown in FIG. 1, the imaging apparatus 15 is a computer tomograph with a circular gantry having a central opening 25. For imaging purposes, the patient 21 is moved into the computer tomograph far enough so that the volume of the patient 21 to be imaged may be imaged.

After the image has been produced, the patient 21 is moved out of the computer tomograph far enough that a rotation of the radiation therapy/imaging apparatus 13, 15 is possible.

The consecutively arranged radiation therapy/imaging apparatus 13, 15 is mounted on a rotatably mounted, circular base plate 27 to implement the rotation. The base plate 27 is embedded in a base 29 such that a continuous transition is produced between the base plate 27 and the base 29.

Figure 2:
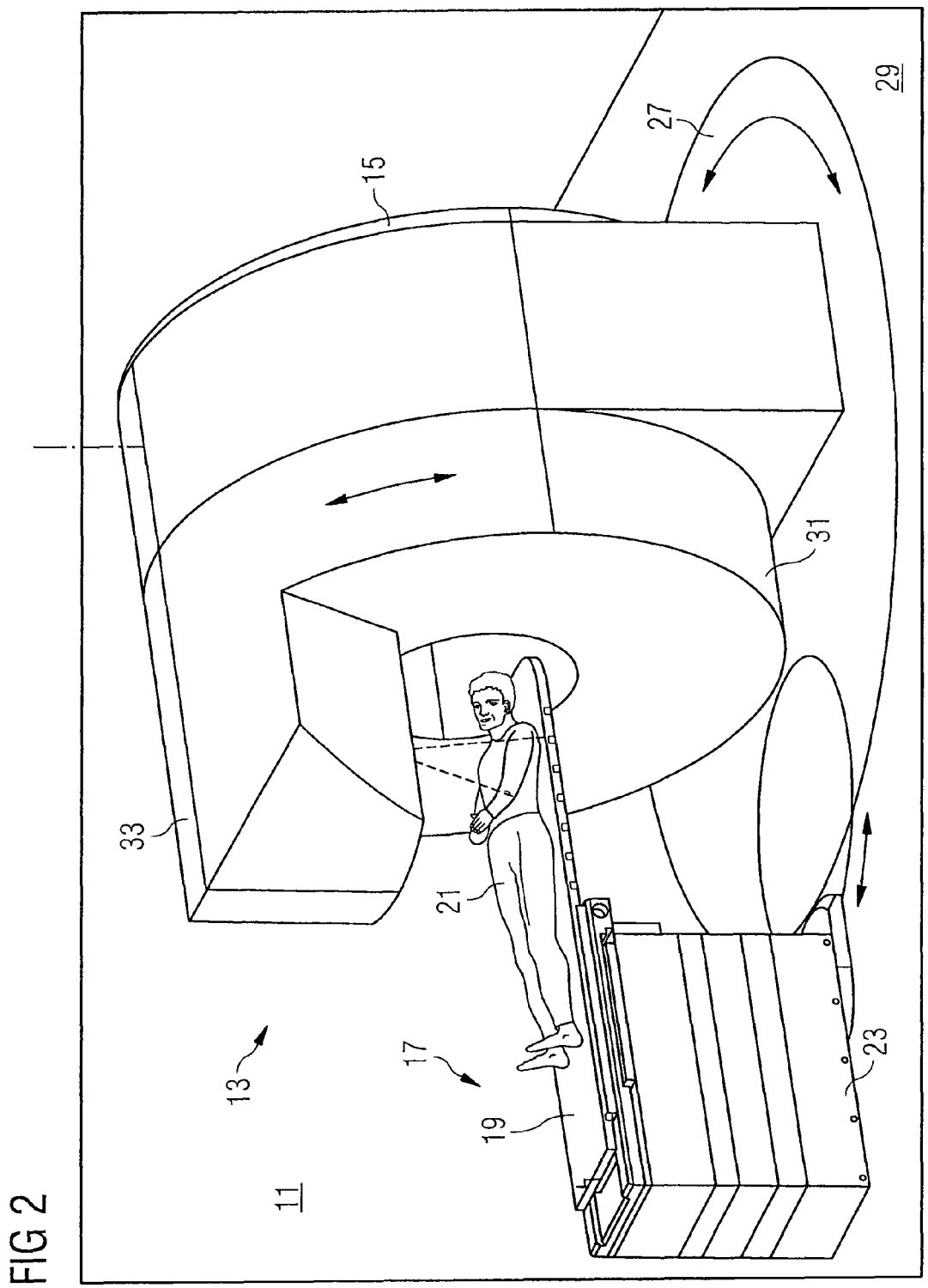
FIG. 2 shows one embodiment of the radiation therapy system in a rotational position for radiation therapy.

FIG. 2 shows the radiation therapy system 11 after rotating the radiation therapy/imaging apparatus 13, 15 by 180° about a shared vertical axis; the radiation therapy apparatus 13 is facing the patient 21.

In the embodiment shown in FIG. 2, the radiation therapy apparatus 13 is an o-shaped gantry 31 with an overhanging arm 33, from which therapeutic radiation is directed at the patient 21. The o-shaped gantry 31 may be rotated about the horizontal longitudinal axis of the o-shaped gantry 31, so that the therapeutic treatment beam may be directed at the patient 21 from several directions.

By moving the patient table 19 along the longitudinal axis of the patient table 19, the patient 21 may be moved toward the radiation therapy apparatus 13 and partially positioned in the opening of the o-shaped gantry 31.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation therapy system comprising:
a radiation therapy apparatus for generating a therapeutic treatment beam to irradiate an object;
an imaging apparatus for generating a medical image of the object; and
a positioning apparatus operable to position the object in the radiation therapy system for irradiation and imaging purposes,
wherein the imaging apparatus and the radiation therapy apparatus are both rotatably mounted so that the object is positioned in a first rotation state in the imaging apparatus and is positioned in a second rotation state in the radiation therapy apparatus,
wherein the imaging apparatus and the radiation therapy apparatus are arranged on a shared, rotatable foot, and
wherein the shared, rotatable foot is operable to rotate about an axis of rotation that passes through the radiation therapy apparatus, the imaging apparatus, or the radiation therapy apparatus and the imaging apparatus.

2. The radiation therapy system as claimed in claim 1, wherein the imaging apparatus is a computer tomograph.

3. The radiation therapy system as claimed in claim 1, wherein the radiation therapy apparatus comprises a circular structure with a central opening, and
wherein the positioning apparatus is operable to move the object partially into the central opening.

4. The radiation therapy system as claimed in claim 1, wherein the radiation therapy apparatus comprises an overhanging arm that is operable to direct the therapeutic treatment beam at the object.

5. The radiation therapy system as claimed in claim 1, wherein the shared, rotatable foot is embedded in a surrounding base.

6. The radiation therapy system as claimed in claim 1, wherein the positioning apparatus is rotatably mounted about a vertical axis on a rotatable foot.

7. The radiation therapy system as claimed in claim 2, wherein the radiation therapy apparatus comprises a circular structure with a central opening, and
wherein the positioning apparatus is operable to move the object partially into the central opening.

8. The radiation therapy system as claimed in claim 2, wherein the radiation therapy apparatus comprises an overhanging arm that is operable to direct the therapeutic treatment beam at the object.

9. The radiation therapy system as claimed in claim 3, wherein the radiation therapy apparatus comprises an overhanging arm that is operable to direct the therapeutic treatment beam at the object.

10. The radiation therapy system as claimed in claim 2, wherein the positioning apparatus is rotatably mounted about a vertical axis on a rotatable foot.

11. The radiation therapy system as claimed in claim 3, wherein the positioning apparatus is rotatably mounted about a vertical axis on a rotatable foot.

12. The radiation therapy system as claimed in claim 4, wherein the positioning apparatus is rotatably mounted about a vertical axis on a rotatable foot.

13. The radiation therapy system as claimed in claim 5, wherein the positioning apparatus is rotatably mounted about a vertical axis on a rotatable foot.

14. The radiation therapy system as claimed in claim 1, wherein the imaging apparatus and radiation therapy apparatus form a single shared unit.

15. A radiation therapy system comprising:
- a radiation therapy apparatus for generating a therapeutic treatment beam to irradiate an object;
- an imaging apparatus for generating a medical image of the object; and
- a positioning apparatus operable to position the object in the radiation therapy system for irradiation and imaging purposes,
- wherein the imaging apparatus and the radiation therapy apparatus are both rotatably mounted so that the object is positioned in a first rotation state in the imaging apparatus and is positioned in a second rotation state in the radiation therapy apparatus,
- wherein the imaging apparatus and the radiation therapy apparatus are arranged on a shared, rotatable foot
- wherein the radiation therapy apparatus and the imaging apparatus are arranged one behind the other such that a channel is formed, the object being movable through the channel.

* * * * *